(12) United States Patent
Block et al.

(10) Patent No.: US 8,079,365 B2
(45) Date of Patent: Dec. 20, 2011

(54) SURGICAL DRAPE WITH POSITION ASSISTING FENESTRATION

(75) Inventors: Carrie Block, Chicago, IL (US); Rogelio Reyes, El Paso, TX (US)

(73) Assignee: Allegiance Corporation, McGaw Park, IL (US)

( * ) Notice: Subject to any disclaimer, the term of this patent is extended or adjusted under 35 U.S.C. 154(b) by 223 days.

(21) Appl. No.: 11/803,396

(22) Filed: May 15, 2007

(65) Prior Publication Data
US 2008/0283064 A1 Nov. 20, 2008

(51) Int. Cl.
*A61B 19/00* (2006.01)
(52) U.S. Cl. .................................. 128/853; 128/849
(58) Field of Classification Search ........... 128/849–856
See application file for complete search history.

(56) References Cited

U.S. PATENT DOCUMENTS

| | | | |
|---|---|---|---|
| 3,800,790 A | 4/1974 | Collins | |
| 3,856,006 A * | 12/1974 | Krzewinski | 128/852 |
| 4,024,862 A * | 5/1977 | Collins | 128/854 |
| 4,378,794 A * | 4/1983 | Collins | 128/853 |
| 4,489,720 A | 12/1984 | Morris et al. | |
| 4,957,120 A | 9/1990 | Grier-Idris | |
| 5,161,544 A | 11/1992 | Morris | |
| 5,222,507 A * | 6/1993 | Taylor | 128/849 |
| 5,345,946 A * | 9/1994 | Butterworth et al. | 128/853 |
| 5,394,891 A | 3/1995 | Mills et al. | |
| 6,199,553 B1 * | 3/2001 | Hafer et al. | 128/849 |
| 2005/0061330 A1 * | 3/2005 | Fenwick et al. | 128/849 |
| 2008/0035159 A1 * | 2/2008 | Perez-Cruet | 128/849 |

* cited by examiner

*Primary Examiner* — Patricia Bianco
*Assistant Examiner* — Keri Nelson
(74) *Attorney, Agent, or Firm* — Arent Fox LLP

(57) ABSTRACT

A surgical drape has a fenestration configured to aid in identifying an anatomical point of interest and positioning the fenestration at the surgical site. In one preferred form, the surgical drape has a chevron-shaped fenestration for positioning the fenestration relative to the xiphoid process region of a patient, which is useful for establishing the sterile field in certain bariatric procedures. An anesthesia screen at a head of the drape extends laterally to the sides of the base sheet forming the fenestration and defines integral arm board covers. The lateral ends of the anesthesia sheet are sealed in part to close the ends of the arm board covers. A secondary base sheet defining a smaller, secondary fenestration is releasably attached to the base sheet so that the fenestrations can be aligned with one another. Various instrument and chord management features are also included. A method of making the drape is also disclosed.

24 Claims, 7 Drawing Sheets

SURGICAL DRAPE WITH POSITION ASSISTING FENESTRATION

CROSS-REFERENCE TO RELATED APPLICATIONS

Not applicable.

STATEMENT OF FEDERALLY SPONSORED RESEARCH OR DEVELOPMENT

Not applicable.

BACKGROUND OF THE INVENTION

1. Technical Field

The present invention relates to the field of medical items used during surgery, and more particularly, to surgical barriers and drapes, and even more particularly to such drapes having fenestrations for accessing the surgical sites.

2. Description of the Related Art

It is well known to cover patients undergoing surgery with surgical drapes to create a sterile barrier around the surgical site. Some surgical drapes have fenestrations, or pre-defined openings, used during the procedures for one of two primary purposes, namely, to give access through the drape to the surgical site or to accommodate a portion of the patient's anatomy. In either case, the fenestration provides an opening in the drape to isolate the surgical site, and thereby create a sterile field between the body portion containing the surgical site and the remainder of the patient's body.

Surgical drapes are generally structured so that the fenestrations, and other openings, are shaped and sized in contemplation of either providing surgical access to a specific anatomical site or accommodating an anatomical feature of the patient. Thus, for example, a fenestration for an arm would be positioned in the drape near the proximal end and offset to one lateral side, and it would be dimensioned according to a standardized arm circumference measurement.

In addition to the general sizing and positioning of the fenestration in the surgical drape, drapes for some surgical procedures require special accommodations. For example, extra large or multiple fenestrations may be needed for procedures requiring multiple surgical sites, such as the multiple instrument entry sites required in certain endoscopic procedures. For example, bariatric procedures typically require six or more incisions, one or more for the camera(s) and the rest for the trocars or other working instruments. In bariatric procedures, it is common for the surgeon to make an incision located according to the position of the xiphoid at the base of the sternum. Others are made in the abdomen relative to the navel or other anatomical features.

The shape of the fenestration can be an important factor, particularly for specialized drapes designed for these types of surgical procedures, so that the appropriate anatomical point of interest can be identified readily and the fenestration can be positioned properly for access to the intended surgical site. Typical surgical drapes with fenestrations for accessing the surgical sites have standard shaped fenestrations, such as generally rectangular or circular. Fenestrations for accommodating anatomical features such as limbs are typically circular.

While rectangular and circular fenestrations are common, it is known for surgical drapes to have other, less standard shaped fenestrations. For example, U.S. Pat. No. 3,800,790 to Collins discloses an elliptical fenestration, and U.S. Pat. No. 4,957,120 to Grier-Idris discloses a racetrack shaped fenestration. U.S. Pat. No. 4,489,720 to Morris, et al. and U.S. Pat. No. 5,394,891 to Mills, et al. both disclose a triangular fenestration. U.S. Pat. No. 5,161,544 to Morris discloses a similar triangular fenestration albeit with rounded corners. These patents largely disregard the configuration of the fenestration itself, instead concentrating on the sealing and construction of the panel in which the fenestration is located, since preventing the sterile field at the surgical site from being compromised is a primary concern and is thus often given a priority in design. Morris, et al. disclose that the fenestration could be any desirable configuration, and merely note without explanation that a triangular fenestration is "particularly useful" in cesarean section procedures (col. 3, lines 9-12).

Hafer, et al. disclose, in U.S. Pat. No. 6,199,553, a drape with a separately attachable absorbent reinforcement pad both of which have a five-sided fenestration. The fenestration in the reinforcement pad is formed by cutting and folding back sections of the pad. The folded back sections of the pad provide a "landing zone" for affixing a fluid collection device to the drape. The bottom surface of the reinforcement pad has a film backing that is more suitable for adhesives such that when the sections are folded back, the film surface faces up and provides a good surface for affixing the fluid collection device. The fenestration of the base sheet of the drape is thus made five-sided or "diamond" shaped merely so that the two fenestrations are the same shape and align after the reinforcement pad is cut and the sections forming the landing zone are folded back.

There is thus a need for a surgical drape having a fenestration configured to aid in locating an anatomical point of interest and positioning the fenestration at the surgical site necessary for a given surgical procedure.

SUMMARY OF THE INVENTION

The invention provides a fenestrated surgical drape in which the fenestration is uniquely configured to aid in locating a specific anatomical point of interest of a patient undergoing a surgical procedure and positioning the fenestration at the surgical site. In one preferred embodiment, the fenestration "points" out the xiphoid process of a patient, which is usable for certain bariatric procedures. The fenestration allows the physician to measure and locate one or more incision sites for endoscopic instruments without exposing more of the patient than necessary or requiring the drape to be repositioned during the procedure. The drape can also provide integral arm board covers with closed ends to further minimize non-surgical site exposure of the patient. A secondary sheet can be included with a secondary fenestration of different size and/or configuration to allow for varied applications of the surgical drape.

Specifically, in one aspect the invention provides a surgical drape having a first end and a fenestration with first and second sides intersecting to form an acute angle therebetween. The intersection of the two sides is proximate the first end of the drape such that when the drape is placed onto the patient with the first end toward a head of the patient, the fenestration is located and oriented so that the apex of the fenestration is proximate a xiphoid process of the patient.

The fenestration can have a chevron configuration at the two intersecting sides. The apex of the fenestration effectively "points" out or locates the xiphoid process, and exposes the point of interest which is the basis for locating one or more incisions made during bariatric procedures. In greater detail, the fenestration can have three, four or more sides. The third side intersects the first side to define an obtuse angle therebetween and the fourth side intersects the second side to define an obtuse angle therebetween. A fifth side can intersect the third and fourth sides to define associated included angles each of at least 90 degrees. The five-sided fenestration with the chevron configuration thus defines the desired surgical field.

The drape can include a base sheet, defining the fenestration, and an end sheet attached to the base sheet at the first end. The base sheet can be rectangular and longer (in the longitudinal dimension) than it is wide (lateral dimension), and the end sheet can also be rectangular, extending laterally farther than the base sheet, in a sort of T shape. The lateral ends of the end sheet then can define integral arm board covers, which are preferably closed at their ends via the joining of segments of folded over longitudinal end edges. The long, lateral edges of the end sheet where the arm board covers are defined can be unjoined so that the drape can be easily draped over and removed from the patient. The inside corners of the drape can be formed by rectangular gusset sheets in which one lateral edge of each gusset sheet is joined to the end sheet and one longitudinal edge of each gusset sheet is joined to the base sheet. Rectangular curtain sheets can also be joined to the longitudinal edges of the base sheet for concealing the side of the patient table.

The drape can also have a secondary base sheet that can be attached to the base sheet or any other sheet of the drape. The secondary base sheet can be fixedly or releaseably attached, for example by an adhesive or a hook and loop fastener, to either side of the drape (adjacent or opposite the patient). This additional sheet defines a secondary fenestration of a different, preferably smaller, size than the fenestration of the base sheet and can be of the same or a different configuration. The secondary sheet can be made to expand in size by way of slits in the secondary base sheet that allow the sheet to be folded back, and thereby widen the secondary fenestration. The secondary base sheet is attached to the patient of the drape so that the secondary fenestration is aligned with the fenestration of the base sheet, thereby allowing the surgical site to be accessed without repositioning the drape.

The drape can also include tabs for engaging wires and other chords associated with surgical instruments and other medical devices used in the surgical theater. Pouches and troughs for surgical instruments and other items can also be attached to the drape, for example to the base sheet adjacent to the fenestration.

Thus, in another aspect the invention provides a surgical drape for covering a patient undergoing a bariatric procedure in which the drape includes an end sheet defining arm board covers, a base sheet attached to the end sheet and defining a multi-sided fenestration with first and second sides intersecting to form an acute angle therebetween with its apex pointed toward the end sheet, and a secondary base sheet defining a secondary fenestration of a smaller size than the fenestration of the base sheet. The secondary base sheet is attached to the one or more sheets of the drape so that the secondary fenestration is aligned with the fenestration of the base sheet. When the drape is placed onto the patient with the end sheet toward a head of the patient the multi-sided fenestration is located and oriented so that the intersection of the first and second sides is proximate a xiphoid process of the patient.

The entire drape, or some of its individual sheets, can be made of a non-woven medical fabric. Additionally, elastomeric films can be employed for certain sheets or combined with the non-woven material in a laminate structure. While the drape of the present invention should not be limited to any particular material construction, the base sheet can be a spunbond-meltblown-spunbond trilaminate. Other sections, such as the end and gusset sheets can be a thinner, and less costly spunbond-meltblown bilaminate. The side curtains can be a simple elastomeric film.

Another aspect of the invention provides a method of making a fenestrated surgical drape for bariatric procedures. The method includes arranging an end sheet of a non-woven laminate material so that its length extends along a lateral axis and its width extends along a longitudinal axis, and arranging a base sheet of non-woven laminate material so that its length extends along the longitudinal axis and its width extends along the lateral axis. Then, the base sheet is joined to the end sheet so a longitudinal edge of the base sheet is connected along an intermediate section of longitudinal edge of the end sheet. A multi-sided fenestration is formed in the base sheet with first and second sides intersecting at an angle therebetween to form an apex pointed toward the end sheet such that when the drape is placed onto the patient with the end sheet toward a head of the patient the multi-sided fenestration is located and oriented so that the intersection of the first and second sides is proximate a xiphoid process of the patient. The method can also include joining lateral end segments of associated end and gusset sheets to close off (at least in part) the ends of the arm board covers.

The above and still other advantages of the invention will be apparent from the detailed description and drawings. What follows are one or more preferred embodiments of the present invention. To assess the full scope of the invention the claims should be looked to as the preferred embodiment(s) are not intended to be exclusively within the scope of the invention.

DETAILED DESCRIPTION OF THE PREFERRED EMBODIMENT(S)

The present invention pertains to a fenestrated surgical drape facilitating the location of key anatomical features and allowing access to the associated surgical site during a surgical procedure. The surgical drape also has an additional sheet providing a secondary fenestration that can overlay the primary fenestration to provide a different opening size and/or configuration. In one preferred embodiment of the invention shown and described in detail herein, the fenestration has an angled, chevron-shaped side that "points" toward the patient's head and registers with the patients xiphoid process from which the position of the fenestration on the patient is based. In this way, the surgeon can readily identify the location of the sterile field as well as the loci for various incisions. By locating the xiphoid process, as well as being of large dimension, the drape is suitable for common bariatric procedures, such as gastric bypass procedures.

Figure 1:
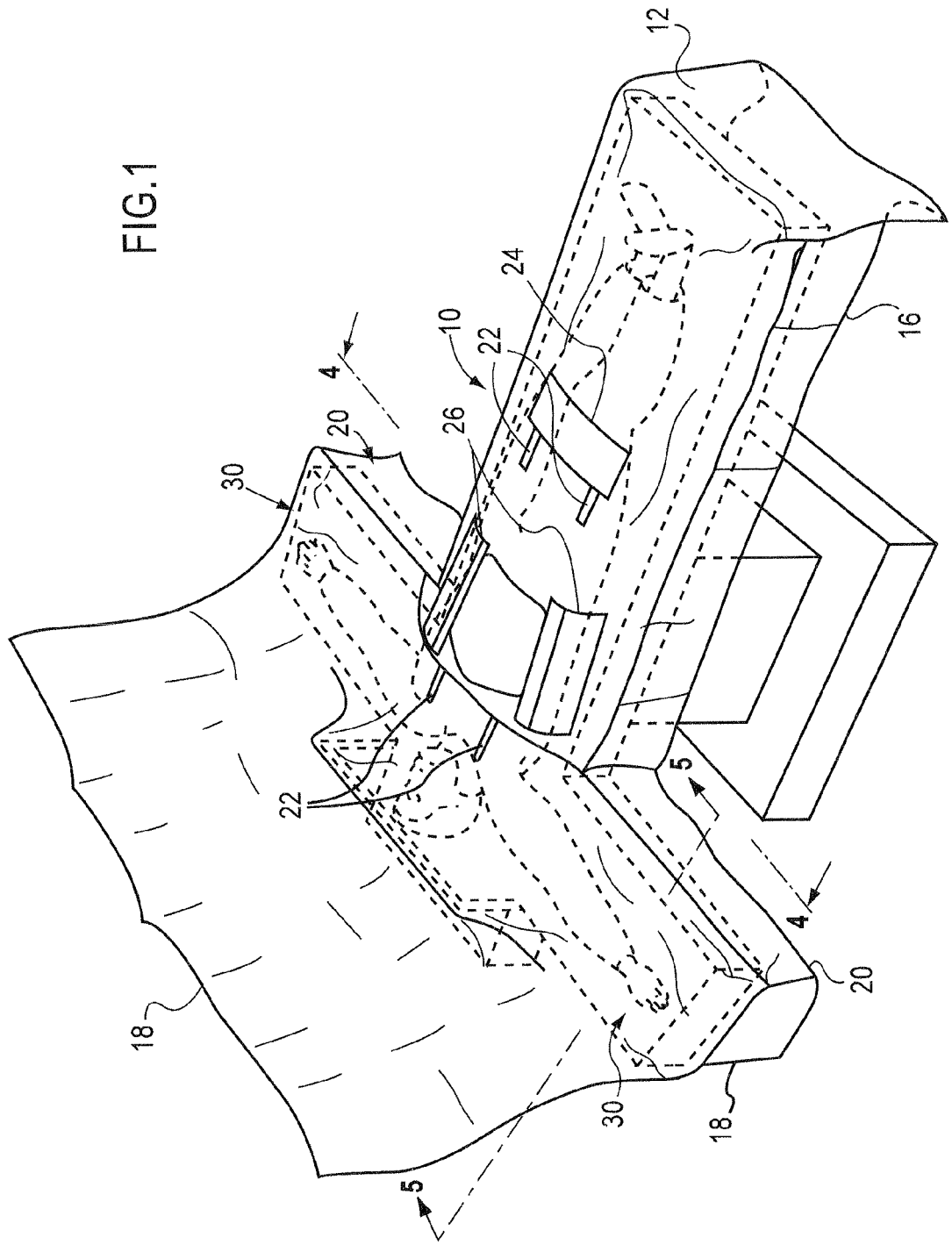
FIG. 1 is a perspective view of a patient on a surgical table draped in a fenestrated surgical drape according to the present invention.

FIG. 1 generally illustrates the surgical drape 10 as would be used during a surgical procedure. The surgical drape 10 overlies a patient laid on an operating table in the supine position. The surgical drape 10 is large enough to cover the patient as well as drape over the table including the foot, head, and arm areas.

Figure 2:
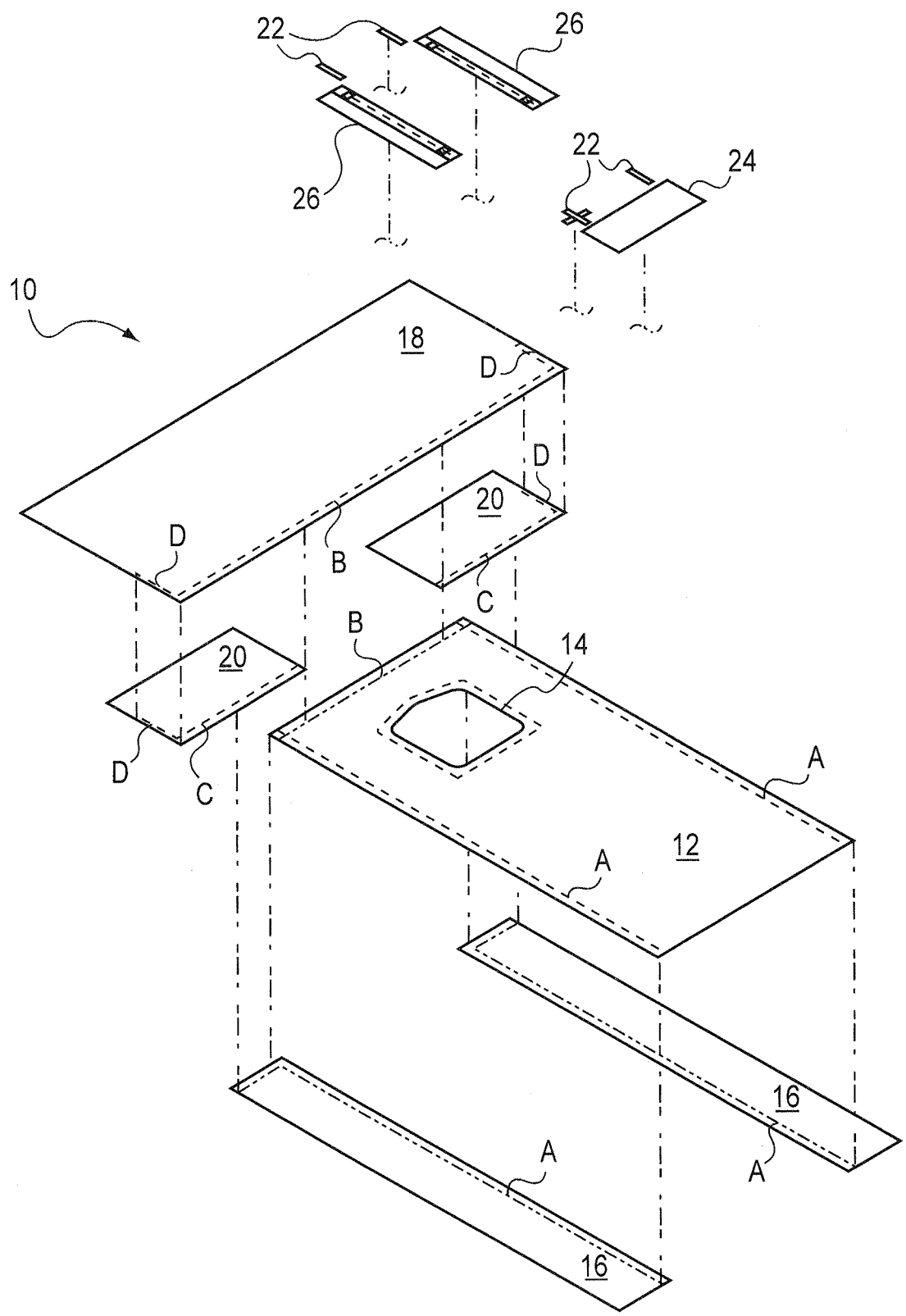
FIG. 2 is an exploded perspective view of the surgical drape shown in FIG. 1.
Figure 3:
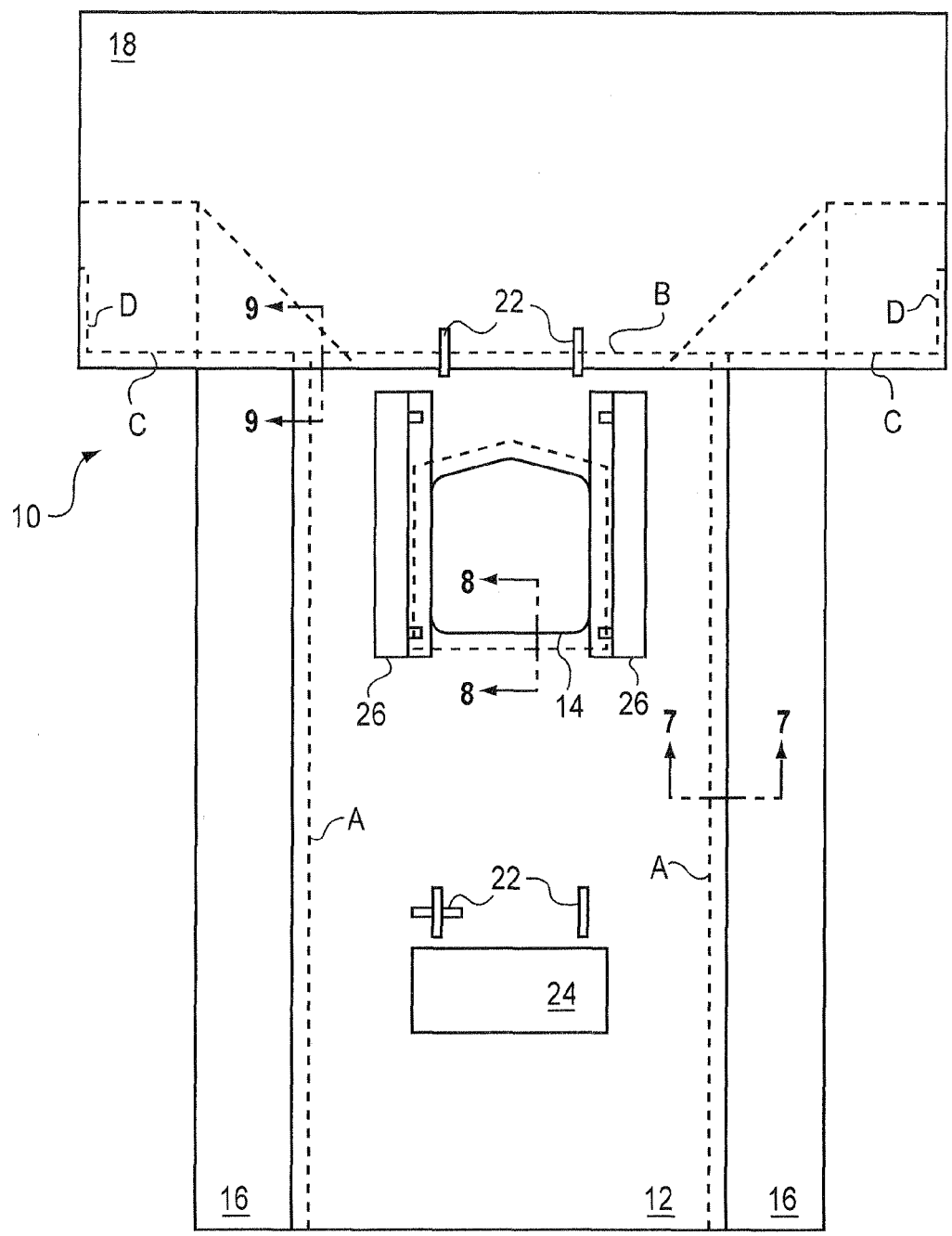
FIG. 3 is a top plan view of thereof.

The construction and components of the surgical drape 10 are shown in FIGS. 2 and 3 exploded and assembled, respectively. The surgical drape 10 has a large base sheet 12 where a fenestration 14 is located. The base sheet 12 is shown rectangular in the illustrated embodiment, but it can be any suitable shape, provided it is large enough to cover a human body or a sufficient portion of the body adjacent the surgical site to assist in creating a sterile field at the surgical site. In the case of the surgical drape 10 being used for a bariatric procedure, the base sheet 12 is preferably oversized to extend an increased dimension necessary to cover larger patients. Along the two long sides of the base sheet 12 are rectangular curtains 16. Extending along and beyond one short end of the base sheet 12 is a rectangular end sheet defining an anesthesia screen 18. Two rectangular gusset sheets 20 extend between the base sheet 12, the anesthesia screen 18 and the associated curtain 20.

Figure 4:
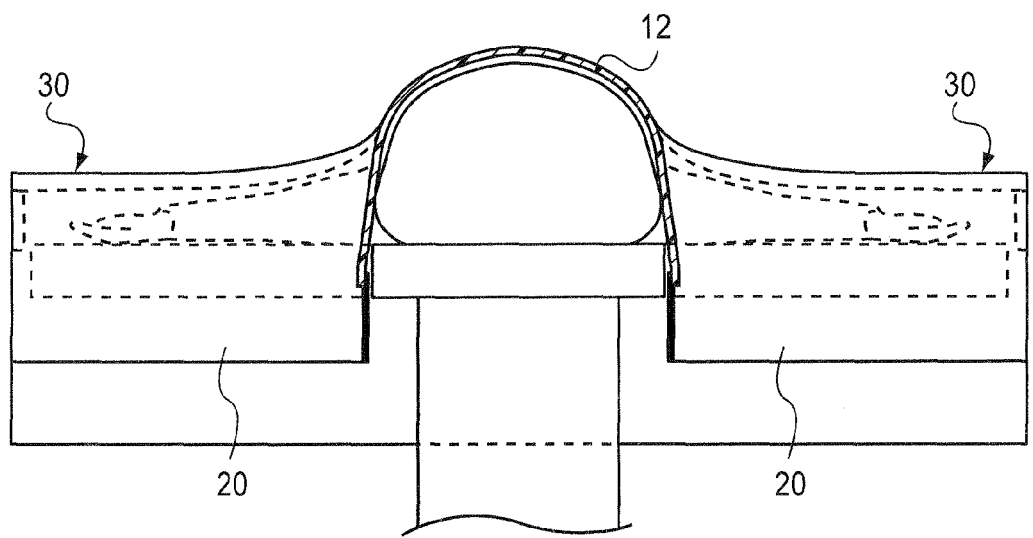
FIG. 4 is a sectional view taken along line 4-4 of FIG. 1 through the fenestration in the surgical drape.
Figure 5:
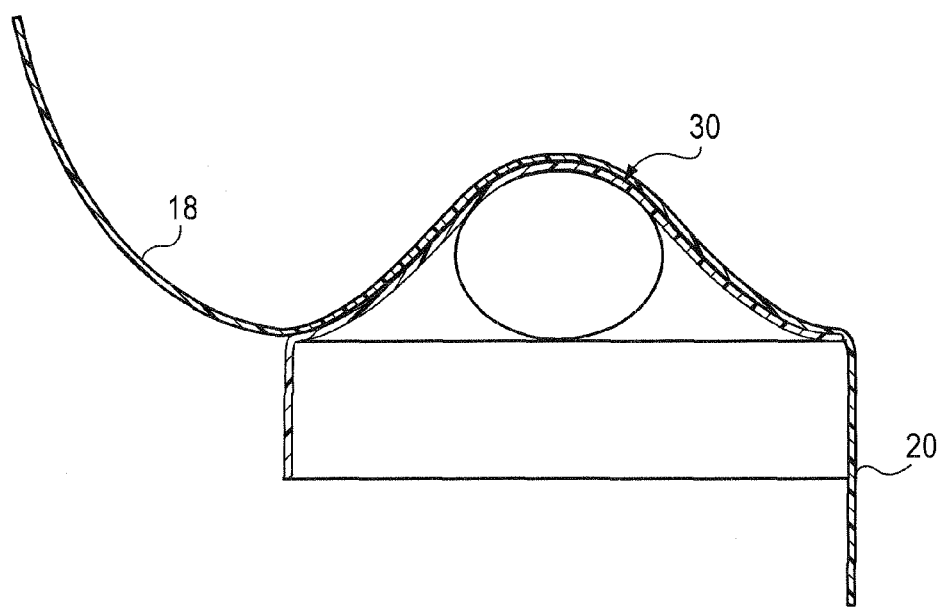
FIG. 5 is a sectional view taken along line 5-5 of FIG. 1 through an arm board cover of the surgical drape.

The surgical drape 10 is formed by joining the sections 12, 16, 18 and 20 along the dashed lines in FIGS. 2 and 3 as follows. Specifically, with reference to FIGS. 2, 3, 7 and 9, each of the curtains 16 is joined along one long edge to one long edge of the base drape 12 along lines A. The anesthesia screen 18 is joined to the base sheet 12 along lines B with the long dimension of the anesthesia screen 18 extending along a lateral axis and its width extending along a longitudinal axis extending in the dimension of the long dimension of the base sheet 12. The gusset sheets 20 are joined along lines C to the lines B of the base sheet 12 and the anesthesia screen 18 so that the outer ends are coterminous with the ends of the anesthesia screen 18. A length of the ends of the gusset sheets 20 and the anesthesia screen 18 are also joined along lines D. As shown in FIGS. 1, 4 and 5, joinder along lines D closes the ends of the sections of the surgical drape 10 that form integral arm board covers 30. The close-ended arm board covers 30 are important to ensure that the patients arms, hands and fingers do not become exposed to the sterile surgical site should the surgical drape 10 shift position during surgery, for example when the surgeon contacts the surgical drape 10 while standing near the patient's chest or abdominal cavity, access to which is facilitated by the arms being extended out at 90 degrees to the torso.

The sections 12, 16, 18 and 20 can be joined along the lines A-D as shown, in spaced apart point contact or line contact, or more preferably in area contact to provide an enhanced connection. Any suitable means can be used, including ultrasonic welding, stitching, adhesive, or other mechanical, thermal or chemical bonding. One suitable technique for joining the sections uses a hot glue gun to apply a hot melt adhesive along the joinder lines.

There are also cord and tube holding tabs 22 affixed to the surgical drape 10 for retaining tubing and/or electrical cords to prevent them from entering the sterile field. In addition, the surgical drape 10 has an instrument pad 24 and a pair of troughs or pouches 26 located at lateral sides of the fenestration 14.

Figure 6:
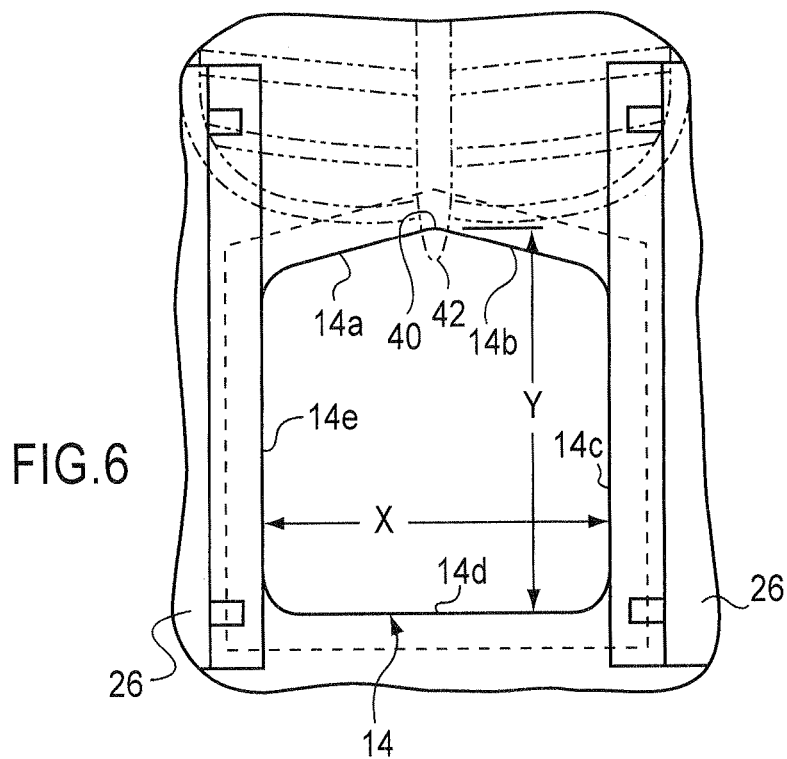
FIG. 6 is an enlarged partial plan view of the fenestration in the surgical drape.
Figure 7:
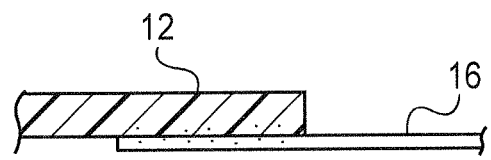
FIG. 7 is a partial section view taken along line 7-7 of FIG. 3 through the seam between a base sheet and a side curtain of the surgical drape.
Figure 8:
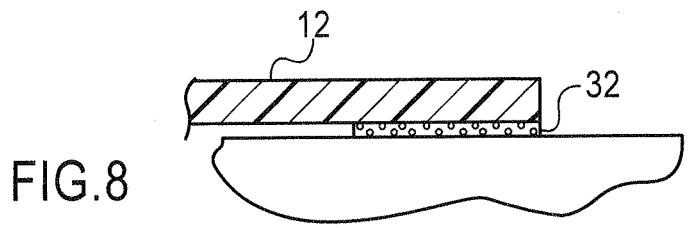
FIG. 8 is a partial section view taken along line 8-8 of FIG. 3 through a side of the fenestration in the base sheet.
Figure 9:
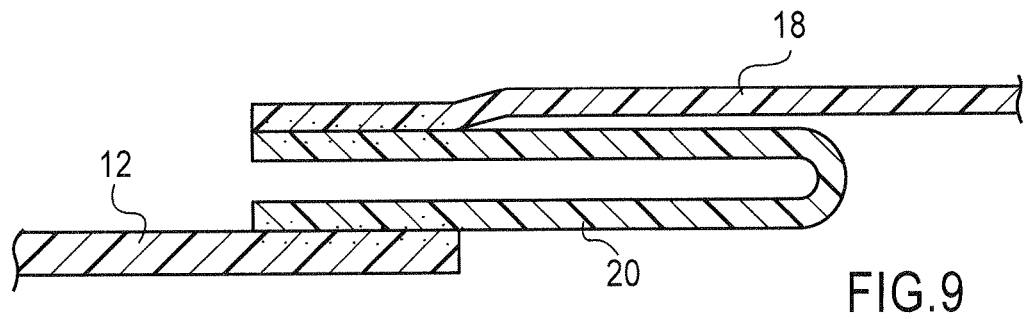
FIG. 9 is a partial section view taken along line 9-9 of FIG. 3 through the connection between the base sheet, an end sheet and a gusset sheet.

As shown in FIGS. 3, 6 and 8, to fix the position of the surgical 10 in the proper position for surgery, a suitable bonding agent or device 32 can be used about the periphery of the fenestration 14 at the underside of the base sheet 12. A suitable bonding device is a double-sided tape with a release liner that can be removed to expose the adhesive. A liquid adhesive or other agent could be used.

The sections 12, 16, 18 and 20, as well as the instrument pad 24 and troughs 26 can be made of any of a variety of suitable commercially available medical fabric materials. Such medical fabric materials known in the surgical field include without limitation non-woven fabrics. "Non-woven fabrics" as used herein refers to a single web, or an assembly or laminate of multiple webs, formed of individual randomly laid fibers, for example using a spunlaid, thermobonded, spunbonded, meltblown or bonded carded web process. A laminate of non-woven fabrics is one conventional material in the surgical field that could be used for the base drape 12. A spunbonded/meltblown/spunbonded laminate of polypropylene fibers is one example. Such a spunbonded/film/spunbonded laminate material is commercially available as Tiburon™ from Ahistrom Corporation of Helsinki, Finland. Another example of a suitable medical fabric material is a combination non-woven fabric and film in which a liquid impervious polymer film is disposed between two non-woven layers. This preferred embodiment is shown in FIG. 6.

In any of composite or laminate sheet construction, the individual web layers can be joined together throughout some or all of the surface area and/or along the periphery using any suitable mechanical, thermal, or chemical bonding process, such as point or pattern bonding by the application of heat and/or pressure to the webs. The fibers comprising the various webs can be hydrophilic (liquid absorbing) or hydrophobic (liquid repelling) depending on the material selected. Particularly when a liquid impervious layer is used, such as an inner polymer film, the outer facing layer can be made of hydrophilic fibers, or treated with a surfactant to be absorbent. When a liquid impervious layer is not used, the exposed outer layer can made of hydrophobic fibers, or treated to be liquid repelling, so that blood or other body fluids present during surgery do not absorb into and migrate through the material into contact with the patient's body. The sections can be constructed of outer webs of different colors or indicia, or a single web with different colors or indicia on each side, to provide visual indication of the difference in material or surface treatments between the sides of the drape. This would help the practitioner identify the proper side to face the patient, for example, if a softer or hydrophobic web was used at the underside of the base drape.

A thin polymeric film, such as made of polyethylene, polypropylene, polyester, polyvinylchloride and combinations thereof, can be used, for example as the curtains 18. The film would be bondable to other chemically compatible polymeric materials, and particularly the non-woven polymer fabrics and elastomers. Polymeric films are also preferable because of their liquid impervious property. Any suitable film thickness can be used with a preferred range being 2-5 mils.

In the preferred embodiment shown in FIGS. 1-3, the surgical drape 10 has the following construction. The base sheet 12 and troughs 26 are the spunbonded/film/spunbonded laminate Tiburon™ material, the anesthesia screen 18 and the gusset sheets 20 are a spunbonded/film and the curtains 16 are a film.

An important aspect of the surgical drape 10 of the present invention is the configuration and location of the fenestration 14. The fenestration 14 may have at least four sides. One preferred embodiment of the fenestration 14 is shown in top view in FIGS. 3 and 6. As can be seen, in this embodiment the periphery of the fenestration 14 has five sides 14a-14e. The corners are slightly rounded, rather than sharp, to eliminate areas of increased stress concentrations that can lead to tearing of the fenestration 14. In the shown embodiment, sides 14c-14e are generally perpendicular to one another, however, they could form non-right angles therebetween, or could even form a continuous curve. Sides 14a and 14b form an oblique angle therebetween and with respect to sides 14c and 14e, respectively, to resemble a "chevron" shape having an apex 40 at the point of intersection between sides 14a and 14b. The apex 40 points toward the anesthesia screen 18 such that when the drape is placed onto the patient with the anesthesia screen 18 along the head and arms of the patient, the fenestration 14 is located and oriented so that the intersection of sides 14a and 14b is at the xiphoid process 42 of the patient. The apex 40 of the chevron thus calls out, or effectively "points" to the key anatomical feature of the patient to properly locate the surgical field and orient the fenestration 14 for surgery. Specifically, for certain bariatric procedures, the apex 40 of the chevron is aligned in registration with the distal tip of the xiphoid process (shown in phantom in FIG. 6 at 42). Sides 14a and 14b can intersect to define an obtuse angle therebetween, which in the shown embodiment, is larger than the angle between each of respective sides 14b and 14c and sides 14a and 14e. Side 14d can intersect sides 14c and 14e to define associated included angles each of at least 90 degrees.

The fenestration 14 is sized in the "x" and "y" dimensions from the apex 40 so that the surgical drape 10 allows the appropriate access to the surgical site, including all incision loci for cameras and instruments. Although dimensions can vary by procedure, 30-50 centimeters in each dimension would be expected for common bariatric procedures.

Thus, the general procedure for using the surgical drape 10 of the present invention according to one embodiment of the invention is as follows. The patient is laid onto an operating table in the supine position in preparation for surgery. The surgical drape 10 is unpackaged, unfolded and laid over the patient with the anesthesia screen 18 extending across the head and arms of the patents, the base sheet 12 extending along the torso and legs of the patient and the curtains 16 hanging down from the patient's sides. The surgical drape 10 is positioned so that the fenestration 14 is over the surgical site. In particular, the apex 40 of the "chevron" is located just over the distal tip of the xiphoid process as shown in FIG. 6, which is located by probing the patient's sternum. The release liner of the adhesive tape 32 can then be removed to fix the position of the fenestration 14 relative to the patient. The arm board covers 30 can then be fit over the patient's arms with the sealed ends enclosing the patient's hands, and the remainder of the surgical drape 10 can be positioned as needed to ensure that the rest of the patient's body is covered, or at least a sufficient portion thereof to provide for a sterile field at the surgical site. If necessary, one or more additional drapes, with or without fenestrations and apertures, may be used to cover other non-surgical areas of the patient.

Figure 10:
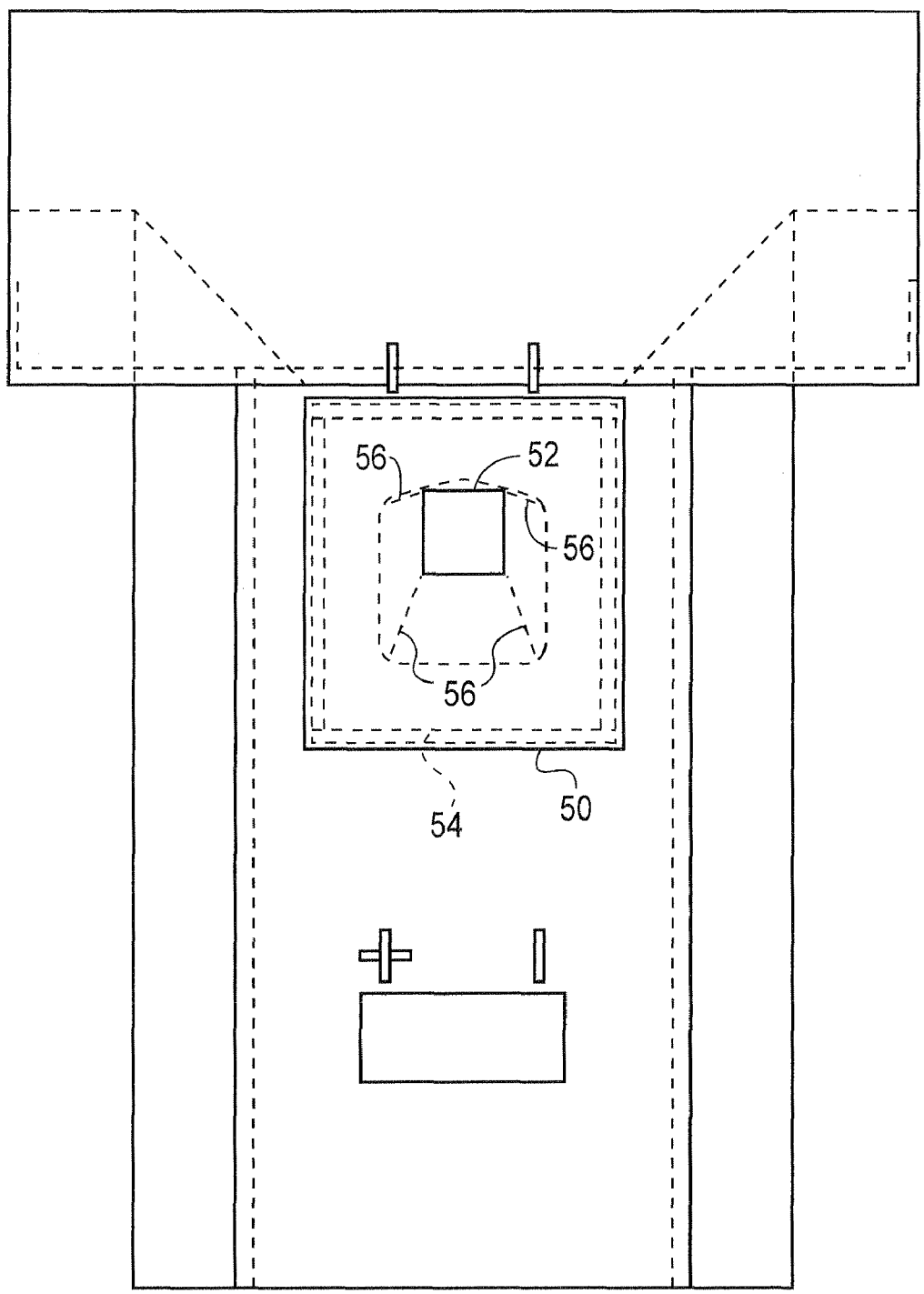
FIG. 10 is a top plan view showing the surgical drape of FIG. 1 with an attachable sheet having a secondary fenestration overlying the fenestration shown in FIG. 1.
Figure 11:
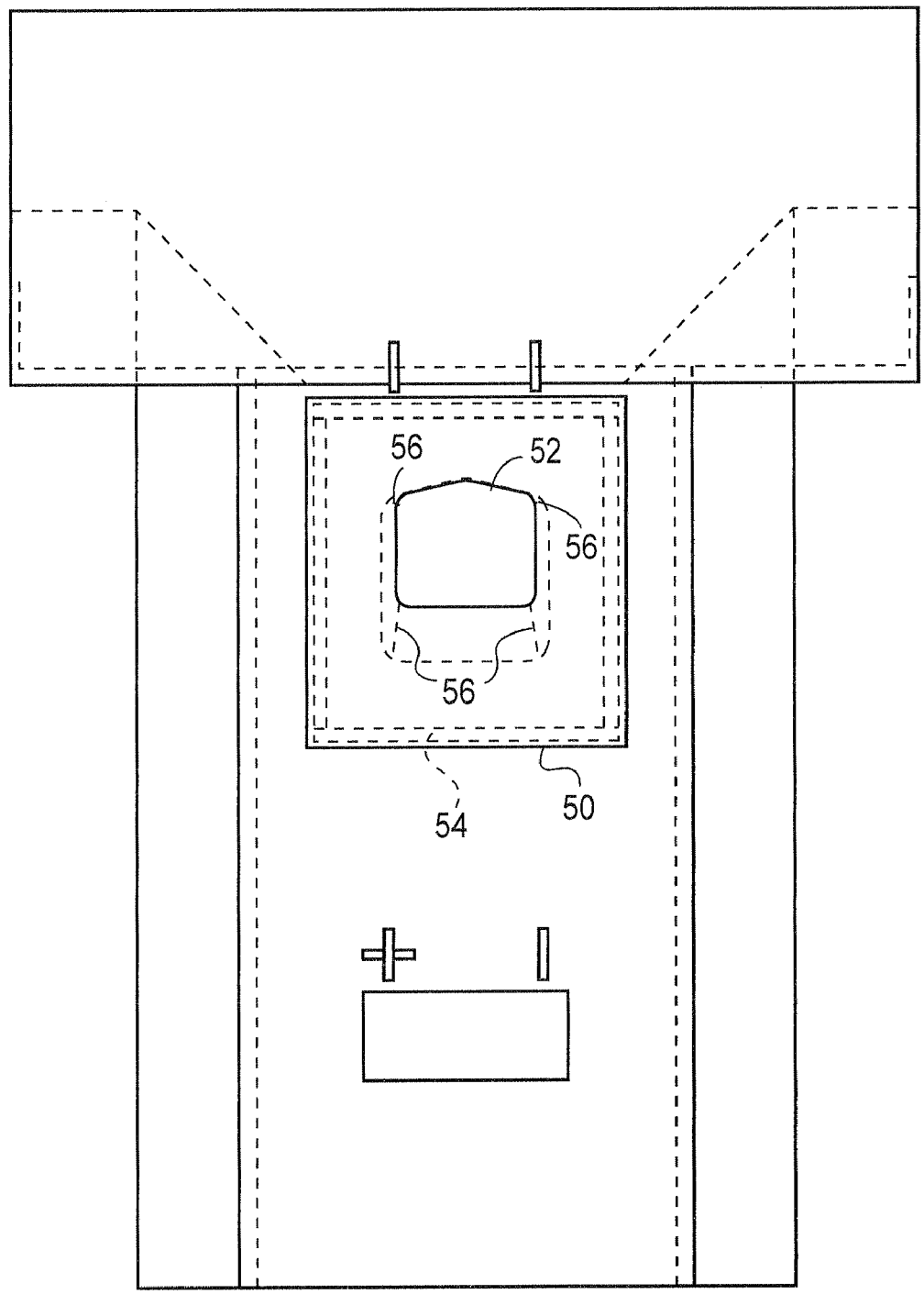
FIG. 11 is a top plan view showing the surgical drape of FIG. 1 with an attachable sheet having a secondary fenestration overlying the fenestration shown in FIG. 1, which is of the same configuration as the fenestration shown in FIG. 1.

In addition, as shown in FIGS. 10 and 11, a secondary base sheet 50 with a secondary fenestration 52 can also be used with the surgical drape 10 shown in FIGS. 1-3. The secondary base sheet 50 is preferably a separate attachable section, for example of Tiburon material, that can be adhered by adhesive tape 54 or otherwise joined to either the base sheet 12 (as shown) or directly to the patient so that the secondary fenestration 52 is in registration with the fenestration 14. The secondary base sheet 50 gives the surgical drape 10 the flexibility of being used for various surgical procedures by virtue of the secondary fenestration 52 being of a different size and/or configuration than the fenestration 14 in the base sheet 12. The secondary fenestration may also have the same configuration as the fenestration 14 of the base sheet 12, as shown in FIG. 11. In the embodiment shown in FIG. 10, the secondary fenestration 52 has a square configuration with side dimensions less than that of the fenestration 14 in the base sheet 12, thus making the surgical drape more amenable for procedures requiring a smaller surgical field. The secondary base sheet 50 can also have predefined score lines 56 allowing the surgeon to vary the opening size and/or configuration of the secondary fenestration 52 to meet the needs of a particular procedure. After tearing or cutting the secondary base sheet 50 along the score lines 56, the resulting flaps can be cut away or simply folded back and secured down to the secondary base sheet 50 by adhesive or other means.

The invention has been described herein with reference to various specific and preferred materials, embodiments and techniques. It should be understood that many modifications and variations to such materials, embodiments and techniques will be apparent to those skilled in the art within the spirit and scope of the invention. Therefore, the invention should not be limited by the above description, and to ascertain the full scope of the invention, the following claims should be referenced.

INDUSTRIAL APPLICABILITY

The invention provides a procedure-specific surgical drape in which the fenestration is configured to aid in identifying a point of interest and positioning the fenestration. Such a surgical drape is particularly useful in surgical procedures for certain endoscopic bariatric procedures.

What is claimed is:

1. A surgical drape for covering a patient undergoing a surgical procedure, the drape having a first end and a primary fenestration therein and a secondary base sheet having a secondary fenestration of a smaller size than the primary fenestration and having predefined score lines that extend outwardly from the perimeter of the secondary fenestration and allow the size and configuration of the secondary fenestration to be varied, the primary fenestration having first and second sides intersecting to form an apex that is proximate the first end of the drape such that when the drape is placed onto the patient in preparation for abdominal surgery with the first end toward a head of the patient, the primary fenestration is located and oriented so that the apex is proximate a xiphoid process of the patient.

2. The surgical drape of claim 1, wherein the primary fenestration has at least four sides.

3. The surgical drape of claim 2, wherein the primary fenestration has third and fourth sides, and wherein the third side intersects the first side to define an obtuse angle therebetween and the fourth side intersects the second side to define an obtuse angle therebetween.

4. The surgical drape of claim 3, wherein the primary fenestration has a fifth side that intersects the third and fourth sides to define associated included angles each of at least 90 degrees.

5. The surgical drape of claim 1, including a primary base sheet, defining the primary fenestration, and an end sheet attached to the primary base sheet at the first end.

6. The surgical drape of claim 5, wherein the primary base sheet has a longitudinal dimension and a lesser lateral dimension, and wherein the end sheet extends laterally to a greater extent than the primary base sheet.

7. The surgical drape of claim 6, wherein lateral ends of the end sheet define integral arm board covers.

8. The surgical drape of claim 7, wherein the arm board covers are closed at their ends.

9. The surgical drape of claim 8, wherein the arm board covers have longitudinal end edges and wherein each end edge is folded into two edge segments with each edge segment overlying and at least in part joined to the other edge segment.

10. The surgical drape of claim 9, wherein the arm board covers have unjoined lateral edges.

11. The surgical drape of claim 10, further including gusset sheets, each having lateral and longitudinal edges, and wherein one lateral edge of each gusset sheet is joined to the end sheet and one longitudinal edge of each gusset sheet is joined to the primary base sheet.

12. The surgical drape of claim 11, wherein the primary base sheet, end sheet and gusset sheets are rectangular.

13. The surgical drape of claim 12, further including at least one of instrument and cord management features attached to the primary base sheet.

14. The surgical drape of claim 5, wherein the secondary base sheet is releasably attachable to the primary base sheet.

15. The surgical drape of claim 5, wherein the primary base sheet is a non-woven material.

16. The surgical drape of claim 15, wherein the primary base sheet is a spunbond meltblown spunbond trilaminate.

17. The surgical drape of claim 15, further including gusset sheets, each having lateral and longitudinal edges,
wherein one lateral edge of each gusset sheet is joined to the end sheet and one longitudinal edge of each gusset sheet is joined to the primary base sheet, and
wherein the end sheet and gusset sheets are a spunbond meltbown non-woven laminate.

18. The surgical drape of claim 1, wherein the secondary base sheet is attachable to the drape so that the secondary fenestration is aligned with the primary fenestration.

19. The surgical drape of claim 18, wherein the secondary fenestration is of the same configuration as the primary fenestration.

20. The surgical drape of claim 1, wherein the first and second sides intersect to form an acute angle.

21. A surgical drape for covering a patient undergoing a bariatric procedure, the drape comprising:
an end sheet defining arm board covers;
a primary base sheet attached to the end sheet and defining a multi-sided fenestration with first and second sides intersecting to form an apex pointed toward the end sheet; and
a secondary base sheet defining a secondary fenestration of a smaller size than the multi-sided fenestration, the secondary base sheet being attachable to one of the end and primary base sheets so that the secondary fenestration is aligned with the multi-sided fenestration and having predefined score lines that that extend outwardly from the perimeter of the secondary fenestration and allow the size and configuration of the secondary fenestration to be varied,
wherein when the drape is placed onto the patient with the end sheet toward a head of the patient, the multi-sided fenestration is located and oriented so that the intersection of the first and second sides is proximate a xiphoid process of the patient.

22. A method of making a surgical drape for bariatric procedures, comprising:
arranging an end sheet of a non-woven laminate material so that its length extends along a lateral axis and its width extends along a longitudinal axis;
arranging a primary base sheet of non-woven laminate material so that its length extends along the longitudinal axis and its width extends along the lateral axis;
arranging a secondary base sheet of non-woven laminate material so that its length extends along the longitudinal axis and its width extends along the lateral axis;
joining the primary base sheet to the end sheet so a longitudinal edge of the primary base sheet is connected along an intermediate section of longitudinal edge of the end sheet;
forming a multi-sided fenestration in the primary base sheet with first and second sides intersecting to form an apex pointed toward the end sheet such that when the drape is placed onto the patient in preparation for abdominal surgery with the end sheet toward a head of the patient the multi-sided fenestration is located and oriented so that the apex is proximate a xiphoid process of the patient;
forming a secondary fenestration of a smaller size than the multi-sided fenestration in the secondary base sheet; and
forming predefined score lines in the secondary base sheet that that extend outwardly from the perimeter of the secondary fenestration and allow the size and configuration of the secondary fenestration to be varied.

23. The method of claim 22, further comprising folding lateral ends of the end sheet and joining the folded edge segments of each lateral end.

24. A method for donning a surgical drape, comprising the step of:
positioning the surgical drape on a patient, the surgical drape having a first end and a primary fenestration therein and a secondary base sheet having a secondary fenestration of a smaller size than the primary fenestration and having predefined score lines that that extend outwardly from the perimeter of the secondary fenestration and allow the size and configuration of the secondary fenestration to be varied, the primary fenestration having first and second sides intersecting to form an apex that is proximate the first end of the drape, such that the apex is configured to lie at a head end of the xiphoid process of the patient, and a side of the primary fenestration opposite the apex is configured to lie at an abdomen end of the xiphoid process of the patient.

* * * * *